United States Patent [19]

Cihonski

[11] 4,246,202
[45] Jan. 20, 1981

[54] PRODUCTION OF CYCLIC HYDROCARBONS FROM NORMAL OCTENES

[75] Inventor: John L. Cihonski, Odessa, Tex.

[73] Assignee: El Paso Products Company, Odessa, Tex.

[21] Appl. No.: 41,681

[22] Filed: May 23, 1979

[51] Int. Cl.³ .................. C07C 85/11; C07C 15/42; C07C 12/46; C07C 5/31
[52] U.S. Cl. .................. 564/423; 585/365; 585/414; 585/418; 585/419
[58] Field of Search .............. 585/414, 365, 418, 419, 585/435; 260/580

[56] References Cited

U.S. PATENT DOCUMENTS

| | | | |
|---|---|---|---|
| 3,308,193 | 3/1967 | Bajars | 585/418 |
| 3,686,341 | 8/1972 | Eberly | 585/420 |

FOREIGN PATENT DOCUMENTS 281455  12/1970  U.S.S.R. .................. 260/580

*Primary Examiner*—John Doll
*Attorney, Agent, or Firm*—Depaoli & O'Brien

[57] ABSTRACT

This invention provides a process for the production of cyclic hydrocarbons from light olefinic hydrocarbons which involves contacting n-octene feed with a Group VIII metal oxide catalyst in the presence of molecular oxygen at temperatures of 130°–500° C. and a pressure of 1–200 psi to yield vinylcyclohexene and ethylbenzene.

The invention further provides a two step vapor phase process embodiment for converting n-octene feed to styrene via a vinylcyclohexene/ethylbenzene intermediate mixture. When nitrobenzene is employed as the oxidizing agent in place of molecular oxygen, aniline is obtained as an additional product.

5 Claims, No Drawings

PRODUCTION OF CYCLIC HYDROCARBONS FROM NORMAL OCTENES

BACKGROUND OF THE INVENTION

Light petroleum fractions from refinery and petrochemical operations constitute a potentially valuable raw material source for the production of styrene and other commercially important aromatic compounds.

Processes for the conversion of light paraffins to aromatic hydrocarbons at some stage usually involve naphthenic compounds. A well-known reaction is the dehydrocyclization of $C_6$ and higher paraffins to aromatic derivatives containing the same number or less carbon atoms than the feed material. Under the severe processing conditions typical of petroleum refinery reforming operations, dehydrogenation and dehydrocyclization conversions of light petroleum mixtures are accompanied by competing isomerization, cracking and coking reaction mechanisms. Efforts to develop economical processes for selective production of naphthene and aromatic products from readily available acyclic hydrocarbon raw materials have encountered many difficulties. An extensive technology has been developed which has endeavored to solve the most serious of the technical problems, and provide valuable naphthene and aromatic products with greater selectivity and efficiency from $C_6$ and higher acyclic hydrocarbons.

U.S. Pat. No. 2,212,026 describes the conversion of n-octane to p-xylene and ethylbenzene at 200° C.–400° C. in the presence of a catalyst mixture of alumina and nickel metal. In a similar process, U.S. Pat. No. 2,217,011 describes the conversion of 1-octyne to o-xylene, and U.S. Pat. No. 2,217,012 discloses the conversion of 1,4-octadiene to o-xylene.

U.S. Pat. No. 2,328,755 describes a process which involves contacting n-octene with silica/alumina hydrogel at 710° F. and atmospheric pressure to yield a mixture of paraffins, naphthenes and aromatic compounds.

U.S. Pat. No. 2,775,631 describes a process which involves the conversion of a normal olefin into an aromatic compound by contacting the olefin and carbon dioxide with a molybdenum oxide catalyst at a temperature of 750°–1100° F.

U.S. Pat. No. 3,202,725 describes a process for producing xylene from $C_8$ acyclic hydrocarbons such as diisobutylene employing a catalysts consisting of chromium oxide on eta alumina.

U.S. Pat. No. 3,308,193 describes a process which involves oxidative dehydrogenation of hydrocarbons to form aromatic compounds. 2-Ethylhexene-1 was contacted with a $Fe_3O_4$/CaO catalyst at 500° C. in the presence of oxygen and steam to yield toluene, ethylbenzene, p-xylene, o-xylene and styrene.

U.S. Pat. No. 3,686,341 describes a process for the aromatization of olefinic hydrocarbons which comprises contacting $C_6$–$C_{12}$ olefinic hydrocarbons at 300° C.–800° C. and 15–150 psi with a catalyst consisting of a chrysotile and a transition metal component selected from Group VIB and Group VIII metals.

U.S. Pat. No. 3,758,600 describes a Group VIB metal oxide deposited on a support comprising a mixture of titania and alumina for use as a catalyst to promote the conversion of paraffins, olefins, cycloparaffins and cycloolefins to aromatics at a temperature of 400° F.–1200° F.

U.S. Pat. No. 3,903,185 describes a method of manufacturing ethylbenzene by catalytic aromatization of the $C_8$-cycloolefins obtained in the dimerization of unsaturated $C_4$-hydrocarbons. The catalyst is a metal and/or metal oxide of sub-groups VI, VII and VIII including the platinum metals.

U.S. Pat. No. 4,056,575 describes a process for the production of aromatic hydrocarbons which involves subjecting an unsaturated hydrocarbon containing at least 6 carbon atoms to aromatization in the presence of a catalyst consisting essentially of gallium deposited on a support.

Other patents relating to the conversion of acyclic hydrocarbons to naphthenes and aromatic compounds include U.S. Pat. Nos. 2,124,584; 2,172,535; 2,271,751; 2,316,271; 2,320,147; 2,336,783; 2,344,318; 2,386,957; 2,394,170; 2,423,176; 2,441,297; 2,508,014; 2,598,642; 2,857,442; 2,992,283; 3,013,089; 3,251,900; 3,325,552; 3,480,684; 3,501,542; 3,548,021; 3,579,598; 3,670,044; 3,719,721; 3,758,600; 3,775,502; 3,981,794; 4,104,320; and the like.

Accordingly, it is an object of this invention to provide an improved process for converting light acyclic hydrocarbons into cyclic hydrocarbons.

It is another object of this invention to provide an improved process for converting n-octenes into naphthenes and aromatic hydrocarbons.

It is a further object of this invention to provide an improved two-step process for converting n-octenes into styrene.

Other objects and advantages shall become apparent from the following description and examples.

DESCRIPTION OF THE INVENTION

One or more objects of the present invention are accomplished by the provision of a process for the production of cyclic hydrocarbons from light acyclic hydrocarbons which comprises contacting n-octene feed with an oxidized Group VIII metal catalyst in the presence of molecular oxygen at a temperature between about 130° C. and 500° C. and a pressure between about 1 and 200 psi to convert the n-octene feed to vinylcyclohexene and ethylbenzene (and styrene). The reaction can be conducted as a batch or continuous process, either in the liquid or vapor phase. As a liquid phase reaction, the process is preferably conducted at a temperature between about 130° C. and 300° C. for a reaction period between about 1 and 10 hours.

In a preferred embodiment, this invention provides a vapor phase process for the production of styrene from light hydrocarbons which comprises the steps of (1) contacting n-octene feed with a Group VIII metal oxide or hydroxide catalyst in the presence of molecular oxygen at a temperature between about 130° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a Group VIII metal oxide or hydroxide catalyst in the presence of molecular oxygen at a temperature between about 150° C. and 300° C. and a pressure between about 1 and 200 psi for a residence time between about 0.1 and 10 seconds to yield styrene product.

The n-octene feedstock is preferably 1-octene, alone or in admixture with 2-octene and/or 3-octene. This invention also contemplates the use of feedstocks which are mixtures of n-octene with other light acyclic hydrocarbons such as butane, n-butenes, isobutane, isobutylene, butadiene, and the like. Butane, n-butenes and butadiene are susceptible to conversion to vinylcyclohexene and ethylbenzene under the conditions of the present invention process. Depending on availability, a n-butene feed can be substituted in part for the n-octene feedstock in the practice of the present invention process for the production of cyclic hydrocarbons.

Suitable reactors for the vapor phase conversion of n-octene include either fixed bed or fluid bed reactors which contain at least one Group VIII metal oxide or hydroxide catalyst component. The gas fed to the reactors comprises n-octene and molecular oxygen to which nitrogen, carbon dioxide, steam or the like may optionally be added as an inert diluent. Unreacted n-octene feed can be recycled in the process if desired.

In the two-step vapor phase process for styrene production described above, the first step reaction is conducted at temperatures between about 130° C. and 500° C., and preferably at a temperature between about 150° C. and 300° C. The residence time (i.e., catalyst contact time) of the feed stream in the first step reaction is between about 0.5 and 20 seconds, and preferably between about 1 and 15 seconds. Residence time refers to the contact time adjusted to 25° C. and atmospheric pressure. The contact time is calculated by dividing the volume of the catalyst bed (including voids) by the volume per unit time flow rate of the feed stream at NTP.

The mixture containing vinylcyclohexene and ethylbenzene which is the effluent from the first step reaction zone can be introduced directly into the second step reaction zone without any fractionation of effluent components. If desired, the vinylcyclohexene and ethylbenzene can be separated from the other components of the effluent mixture in an essentially pure state. The vinylcyclohexene and ethylbenzene can then be vaporized, admixed with molecular oxygen, and entered into the second step reaction zone to produce the product styrene.

The pressure utilized in the two step vapor phase process can be subatmospheric, atmospheric or superatmospheric. A preferred pressure for the vapor phase process is one which is in the range between about 1 and 200 psi.

In any of the embodiments of the present invention process, the quantity of molecular oxygen (or its equivalent) introduced into the dehydrocyclodimerization reaction system theoretically should be at least sufficient to satisfy the stoichiometry of the oxidative conversions. The molar ratio of oxygen to 1-octene feed can vary broadly over the range between about 0.1:1 and 10:1. A molar ratio of oxygen to 1-octene of about 1:1 has been found to be convenient and effective.

It is not necessary to use pure oxygen as the source of oxygen. Air is a suitable source of oxygen and is desirable for reasons of economy. Alternatively, the oxidizing agent can be ozone (under conditions which prevent direct interaction of ozone and olefin) or a compound which can generate oxygen under reaction conditions (e.g., peroxides and hydroperoxides), or it can be a compound which contains an active-oxygen functional group (e.g., nitro derivatives). Aliphatic and aromatic nitro compounds which have a boiling point below about 250° C. are particularly useful as an oxidizing agent in place of molecular oxygen in the invention process.

Thus, in another embodiment this invention provides a process for the production of styrene and aniline which comprises contacting n-octene feed with a Group VIII metal oxide or hydroxide catalyst in the presence of nitrobenzene at a temperature between about 200° C. and 500° C. and a pressure between about 1 and 200 psi to yield styrene and aniline product.

In a further embodiment, this invention provides a vapor phase process for the production of styrene and aniline which comprises contacting n-octene feed with a Group VIII metal oxide or hydroxide catalyst in the presence of molecular oxygen at a temperature between about 200° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a Group VIII metal oxide or hydroxide catalyst in the presence of nitrobenzene at a temperature between about 200° C. and 300° C. and a pressure between about 1 and 200 psi for a residence time between about 0.1 and 10 seconds to yield styrene and aniline product.

The catalyst employed in the invention process is selected from one or more Group VIII metals which are in an oxidized state (e.g., an oxide or a hydroxide). The preferred Group VIII metals are nickel, palladium and platinum, with palladium being the most preferred Group VIII metal species. Optionally, the catalyst can contain other metallic components such as molybdenum, tungsten, bismuth, vanadium, and the like.

The catalyst can be prepared by adding an alkali (e.g., sodium or potassium hydroxide) to a solution of one or more water soluble Group VIII metal compounds, such as the chlorides, nitrates and sulfates of nickel, palladium and platinum. The precipitate which forms is recovered, washed with water, and dried.

It has been found that the activity of the catalyst is enhanced if the prepared catalyst is calcined in air at a temperature between about 250° C. and 500° C. for a period of about 1–24 hours.

The Group VIII metal oxide or hydroxide composition described can be used as the catalyst per se, but it is preferred that the said composition is combined with a suitable internal diluent or carrier substrate.

The carrier substrate should be relatively refractory to the conditions utilized in the invention process. Suitable carrier substrate materials include (1) silica or silica gel, silicon carbide, clays, and silicates including those synthetically prepared and naturally occurring, which may or may not be acid treated such as attapulgus clay, china clay, diatomaceous earth, Fuller's earth, kaolin, asbestos and kieselguhr; (2) ceramics, porcelain, crushed firebrick and bauxite; (3) refractory inorganic oxides such as alumina, titanium dioxide, zirconium dioxide, chromium oxide, beryllium oxide, vanadium oxide, cesium oxide, hafnium oxide, zinc oxide, molybdenum oxide, bismuth oxide, tungsten oxide, uranium oxide, magnesia, boria, thoria, silica-alumina, silica-magnesia, chromia-alumina, alumina-boria and silica-zirconia; (4) crystalline zeolitic alumino-silicates such as naturally occurring or synthetically prepared mordenite and/or faujasite, either in the hydrogen form or in a form which has been treated with multivalent cations; and (5) spinels such as $MgAl_2O_4$, $FeAl_2O_4$, $ZnAl_2O_4$, $MnAl_2O_4$, $CaAl_2O_4$, and other like compounds having the formula MO.Al$_2$O$_3$ where M is a metal having a valence of 2.

The catalyst as employed in the invention process can be in the shape of granules, pellets, extrudate, powders, tablets, fibers, or other such convenient physical form.

The following examples are further illustrative of the present invention. The reactants and other specific ingredients are presented as being typical, and various modifications can be derived in view of the foregoing disclosure within the scope of the invention.

EXAMPLE I

This Example illustrates the preparation of an oxidation catalyst, and its application in the conversion of n-octene feed to cyclic hydrocarbons.

A catalyst precursor is prepared by admixing 100 grams of water, 4.5 grams of molybdic acid [H$_2$MoO$_4$], 12 grams of bismuth nitrate [Bi(NO$_3$)$_3$. 5H$_2$O], 1 grams of palladium nitrate [Pd(NO$_3$)$_2$] and 10 grams of asbestos. The admixture is heated at 100° C. for 1–2 hours until a thick paste is obtained, and then it is dried in a vacuum oven at 110° C. for 12–18 hours.

The dried catalyst precursor material is powdered and calcined for 5 hours at 500° C. in air. The calcined composition is crushed to provide 20–30 mesh catalyst particles. About 10 cm$^3$ (6–7 grams) of the catalyst composition are charged into a 1 inch I.D. stainless steel tube reactor.

A gaseous feed is prepared by admixing 1-octene and air in proportions which provide about a 4:1 molar ratio of molecular oxygen to 1-octene.

The feed mixture is passed through the tube reactor at a temperature of about 320° C. under autogenous pressure at a rate providing a 1-octene liquid hourly space velocity (LHSV) of 0.6.

The conversion of 1-octene is 16.2 percent and the conversion efficiency (i.e., selectivity), based on the total weight of liquid conversion product, is 41 weight percent vinylcyclohexene, 17 weight percent ethylbenzene, 23 weight percent styrene, 7 weight percent xylene, and 6 weight percent n-octene.

The liquid product mixture is vaporized and mixed with air in about a 1:1 molar ratio of hydrocarbons to molecular oxygen, and passed through a tube reactor containing the same type of Pd/Bi/Mo oxides on asbestos catalyst described above.

The second step dehydrogenation reaction is conducted at a temperature of about 350° C. under autogenous pressure with a LHSV of about 1.0.

The average single pass conversion of ethylbenzene and vinylcyclohexene is in the range of 15–25 percent, and the resultant product mixture consists mainly of unreacted vinylcyclohexene and ethylbenzene, and it contains styrene as the sole product of the conversion reaction. The product mixture contains minor quantities of xylene, n-octane and other liquid byproducts formed in the first step 1-octene oxidation reaction, as well as some unreacted 1-octene.

Alternatively, the liquid product effluent from the first step oxidation reaction zone can be fractionated first. The unreacted 1-octene fraction is recycled to the first step oxidation reaction zone, and the combined vinylcyclohexene and ethylbenzene fractions are vaporized and blended with air and passed through the second step oxidation reaction zone.

EXAMPLE II

This Example further illustrates the conversion of 1-octene into cyclic hydrocarbons.

A feed mixture of oxygen/1-octene (2:1 mole ratio) is passed through a tube reactor under autogenous pressure at a LHSV of 0.8 of 1-octene in contact with a palladium catalyst to yield a product mixture as indicated in the following table.

| T, °C. | % | PdO . H$_2$O/ carrier | % Conv. | Selectivity Octane | Octenes | VCH | EB |
|---|---|---|---|---|---|---|---|
| 260 | 0.1 | Girdler T-372 | 38.5 | 7.0 | 79.0 | 10.0 | 4.0 |
| 165 | 2.0 | Linde 5A zeolite, vac. dried | 100.0 | 2.6 | 92.9 | 2.6 | 2.8 |
| 165 | 2.0 | J. T. Baker 3A zeolite, 300° C. calcin. | 21.5 | 6.5 | 74.4 | 15.8 | 3.3 |
| 202 | 2.0 | J. T. Baker 3A zeolite, 300° C. calcin. | 59.1 | 10.7 | 78.5 | 8.1 | 2.7 |

The octenes in the product mixture are a mixture of 2-octene and 3-octene. The designation EB represents ethylbenzene. VCH refers to vinylcyclohexene type compounds which include the following structures:

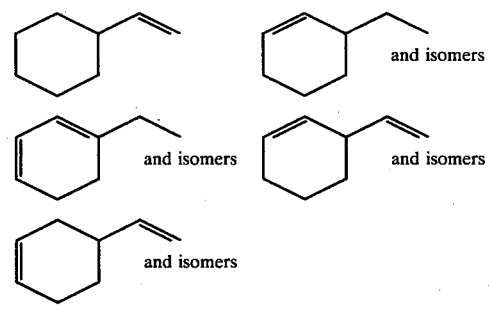

In the manner previously described, the ethylbenzene and vinylcyclohexene components of the product mixture can be converted to styrene in a second step dehydrogenation reaction in the presence of molecular oxygen (or nitrobenzene) and a Group VIII metal catalyst.

EXAMPLE III

Following the same procedure and employing the same type of catalyst system as described in Example I, 1-octene is dehydrocyclodimerized to styrene employing nitrobenzene as the oxidizing component instead of molecular oxygen.

The nitrobenzene is employed in an approximately equimolar quantity relative to the n-octene feed.

The Pd/Bi/Mo oxides on asbestos catalyst bed in the reactor is divided into two zones. In the first zone the temperature is maintained in the range of 250°–300° C., and in the second zone the temperature is maintained in the range of 200°–250° C. The contact time in each zone is about 10 seconds.

The average conversion of 1-octene is about 10 percent per single pass. The resultant liquid product mixture consists of about 45 weight percent each of styrene and aniline and 10 weight percent of byproducts, exclusive of unreacted 1-octene and nitrobenzene.

In a preferred embodiment, molecular oxygen is employed as the oxidizing agent in the first step of the process, and nitrobenzene is used in the second step without the presence of molecular oxygen.

What is claimed is:

1. A process for the production of cyclic hydrocarbons from light acyclic hydrocarbons which comprises contacting n-octene feed with an oxidized palladium metal catalyst in the presence of molecular oxygen at a temperature between about 130° C. and 500° C. and a pressure between about 1 and 200 psi to convert n-octene to vinylcyclohexene and ethylbenzene.

2. A process in accordance with claim 1 wherein the palladium metal catalyst is supported on a carrier substrate.

3. A vapor phase process for the production of styrene from light hydrocarbons which comprises the steps of (1) contacting n-octene feed with a palladium metal oxide or hydroxide catalyst in the presence of molecular oxygen at a temperature between about 130° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a palladium metal oxide or hydroxide catalyst in the presence of molecular oxygen at a temperature between about 150° C. and 300° C. and a pressure between about 1 and 200 psi for a residence time between about 0.1 and 10 seconds to yield styrene product.

4. A process for the production of styrene and aniline which comprises contacting n-octene feed with a palladium metal oxide or hydroxide catalyst in the presence of nitrobenzene at a temperature between about 200° C. and 500° C. and a pressure between about 1 and 200 psi to yield styrene and aniline product.

5. A vapor phase process for the production of styrene and aniline which comprises contacting n-octene feed with a palladium metal oxide or hydroxide catalyst in the presence of molecular oxygen at a temperature between about 200° C. and 500° C. and a pressure between about 1 and 200 psi for a residence time between about 0.5 and 20 seconds to produce an effluent mixture containing vinylcyclohexene and ethylbenzene, and (2) contacting the effluent mixture with a palladium metal oxide or hydroxide catalyst in the presence of nitrobenzene at a temperature between about 200° C. and 300° C. and a pressure between about 1 and 200 psi for a residence time between about 0.1 and 10 seconds to yield styrene and aniline product.

* * * * *